(12) United States Patent
Itsumi et al.

(10) Patent No.: US 8,448,517 B2
(45) Date of Patent: May 28, 2013

(54) SHEET PROCESSING DEVICE

(75) Inventors: Kazuhiro Itsumi, Tokyo (JP); Takahiro Yamamoto, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 317 days.

(21) Appl. No.: 12/883,646

(22) Filed: Sep. 16, 2010

(65) Prior Publication Data

US 2011/0226061 A1     Sep. 22, 2011

(30) Foreign Application Priority Data

Mar. 18, 2010 (JP) ................................. 2010-062864

(51) Int. Cl.
*G01N 29/07* (2006.01)
*G01N 29/27* (2006.01)

(52) U.S. Cl.
USPC ................................. 73/597; 73/599; 73/159

(58) Field of Classification Search
USPC .................. 73/104, 105, 159, 599, 600, 597, 73/598
See application file for complete search history.

(56) References Cited

U.S. PATENT DOCUMENTS

| | | | | |
|---|---|---|---|---|
| 4,366,712 A * | 1/1983 | Bathmann et al. | ............... | 73/600 |
| 4,519,249 A * | 5/1985 | Hunt | ............... | 73/596 |
| 5,621,173 A * | 4/1997 | Knorr | ............... | 73/610 |
| 5,652,388 A * | 7/1997 | Callan et al. | ............... | 73/628 |
| 5,922,960 A * | 7/1999 | Toda | ............... | 73/597 |
| 6,745,628 B2 * | 6/2004 | Wunderer | ............... | 73/579 |
| 7,357,027 B2 * | 4/2008 | Haque et al. | ............... | 73/597 |
| 2003/0183012 A1 * | 10/2003 | Wunderer et al. | ............... | 73/602 |
| 2007/0251311 A1 * | 11/2007 | Schoen | ............... | 73/159 |
| 2010/0314300 A1 | 12/2010 | Itsumi et al. | | |
| 2011/0001285 A1 | 1/2011 | Yamamoto et al. | | |

FOREIGN PATENT DOCUMENTS

| | | |
|---|---|---|
| JP | 2008207885 | 9/2008 |
| WO | 2008081183 | 7/2008 |

* cited by examiner

*Primary Examiner* — Peter Macchiarolo
*Assistant Examiner* — Rose M Miller
(74) *Attorney, Agent, or Firm* — Turocy & Watson, LLP

(57) ABSTRACT

According to one embodiment, there is provided with sheet processing device including an ultrasonic wave generator, a detecting array and a judging unit. The ultrasonic wave generator irradiates ultrasonic waves to a sheet being conveyed, from one side of the sheet. The detecting array is arranged in the other side of the sheet and detects sound pressure of the ultrasonic waves passing through the sheet. The judging unit judges a state of the sheet by comparing a predetermined standard value with the sound pressure.

2 Claims, 3 Drawing Sheets

SHEET PROCESSING DEVICE

CROSS REFERENCE TO RELATED APPLICATIONS

This application is based upon and claims the benefit of priority from the prior Japanese Patent Application No. 2010-062864, filed on Mar. 18, 2010, the entire contents of which are incorporated herein by reference.

FIELD

Embodiments described herein relates to a sheet processing device for detecting a foreign material adhering to a sheet like a paper sheet.

BACKGROUND

In sheets processed and printed in a predetermined way, a sheet having a tape stuck thereon to mend a breakage or having a partially lost part by tearing is not suitable for distribution and thus should be separated. Accordingly, an inspection device and a sort counter for the sheets require a mechanism and a method for separating unsuitable sheets by detecting and judging which sheet has a foreign material such as a tape or a lost part. In order to solve this problem, there is a method for identifying a foreign material adhering to a sheet by irradiating ultrasonic waves to the sheet in order to measure the attenuation of the ultrasonic waves passing through the sheet.

However, detection sensitivity of the conventional detection method is not enough to correctly detect a small foreign material or a small lost part.

DETAILED DESCRIPTION

According to one embodiment, there is provided with a sheet processing device including an ultrasonic wave generator, a detecting array and a judging unit.

The ultrasonic wave generator irradiates ultrasonic waves to a sheet being conveyed, from one side of the sheet.

The detecting array is arranged in the other side of the sheet and detects sound pressure of the ultrasonic waves passing through the sheet.

The judging unit judges a state of the sheet by comparing a predetermined standard value with the sound pressure.

In the following, embodiments will now be in detail explained with reference to the accompanying drawings.

First Embodiment

Figure 1:
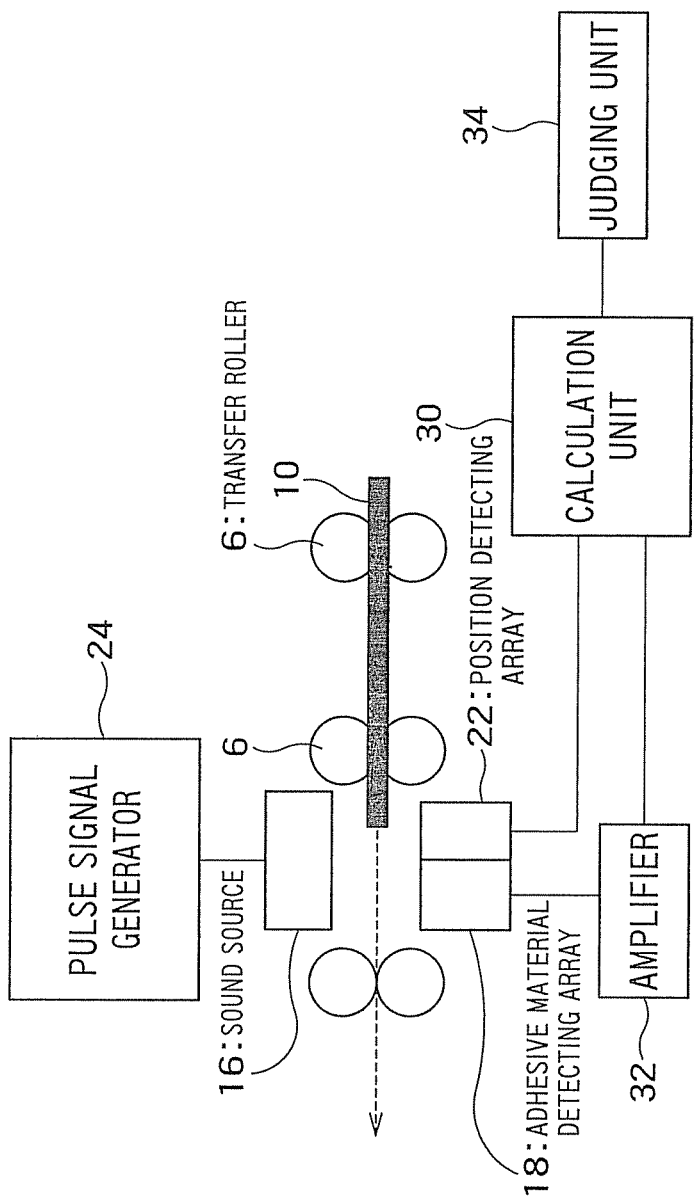
FIG. 1 is a block diagram schematically showing a sheet processing device according to a first embodiment.

FIG. 1 shows a schematic structure of a sheet processing device for detecting a foreign material adhering to a sheet according to a first embodiment. As shown in FIG. 1, the sheet processing device has a sound source 16 for irradiating ultrasonic waves to a sheet 10 to be conveyed. The sound source 16 generates ultrasonic waves corresponding to a signal transmitted from a pulse signal generator 24 and irradiates the ultrasonic waves to the sheet 10 which is conveyed, with its flatness being kept, in the direction of arrow by a conveyance mechanism formed of a plurality of conveyance rollers 6. An ultrasonic transducer such as a piezoelectric vibrator can be used as the sound source 16.

The sheet processing device has a detecting array 18 for detecting the sound pressure of ultrasonic waves passing through the sheet 10. The detecting array 18 is arranged to face the sound source 16 via a conveyance path (shown by a dotted line) along which the sheet 10 is conveyed. As the detection array 18, an ultrasonic transducer, for example, can be used to convert the sound pressure of received ultrasonic waves into an electrical signal corresponding to the magnitude of the ultrasonic waves. It is also possible to form the detecting array 18 by using, instead of the ultrasonic transducer, a microphone. Alternatively, the detecting array 18 is arranged as a displacement meter for measuring vibrations as displacement by using interfering light and detecting the amplitude of the sheet 10 in the thickness direction instead of the sound pressure of vibration sound.

Note that since the sheet 10 is previously processed and printed in a predetermined way, detected sound pressure etc. is different corresponding to each detection part even when the sheet 10 is standard (unused).

A position detecting array 22 is arranged on the upper side in the conveyance direction of the sheet 10, when viewed from an adhesive material detecting array 18. For example, the position detecting array 22 can be formed similarly to the adhesive material detecting array 18. The position detecting array 22 detects that the received sound pressure of the ultrasonic waves generated by the sound source 16 is suddenly reduced as soon as the sheet 10 proceeds (comes) into the detection area. This information is transmitted to a calculation unit 30 which can calculate the time elapsed after the received sound pressure is changed (i.e., reduced), and thus a detected part or a detected position of the sheet 10 by the adhesive material detecting array 18 can be grasped.

Further, the ultrasonic waves detected by the detecting array 18 are amplified by an amplifier 32, and are subjected to calculation processing by the calculation unit 30. The calculation unit 30 previously stores information of normal sound pressure which should be detected in each part of the sheet 10 in an unused state, and calculates the difference between the normal sound pressure information thus stored and the sound pressure information detected by the adhesive material detecting array 18 with respect to each part. A judging unit 34 judges, based on the calculation result transmitted thereto, whether or not the sheet 10 has an adhesive material or a lost part and is suitable for distribution.

Figure 2:
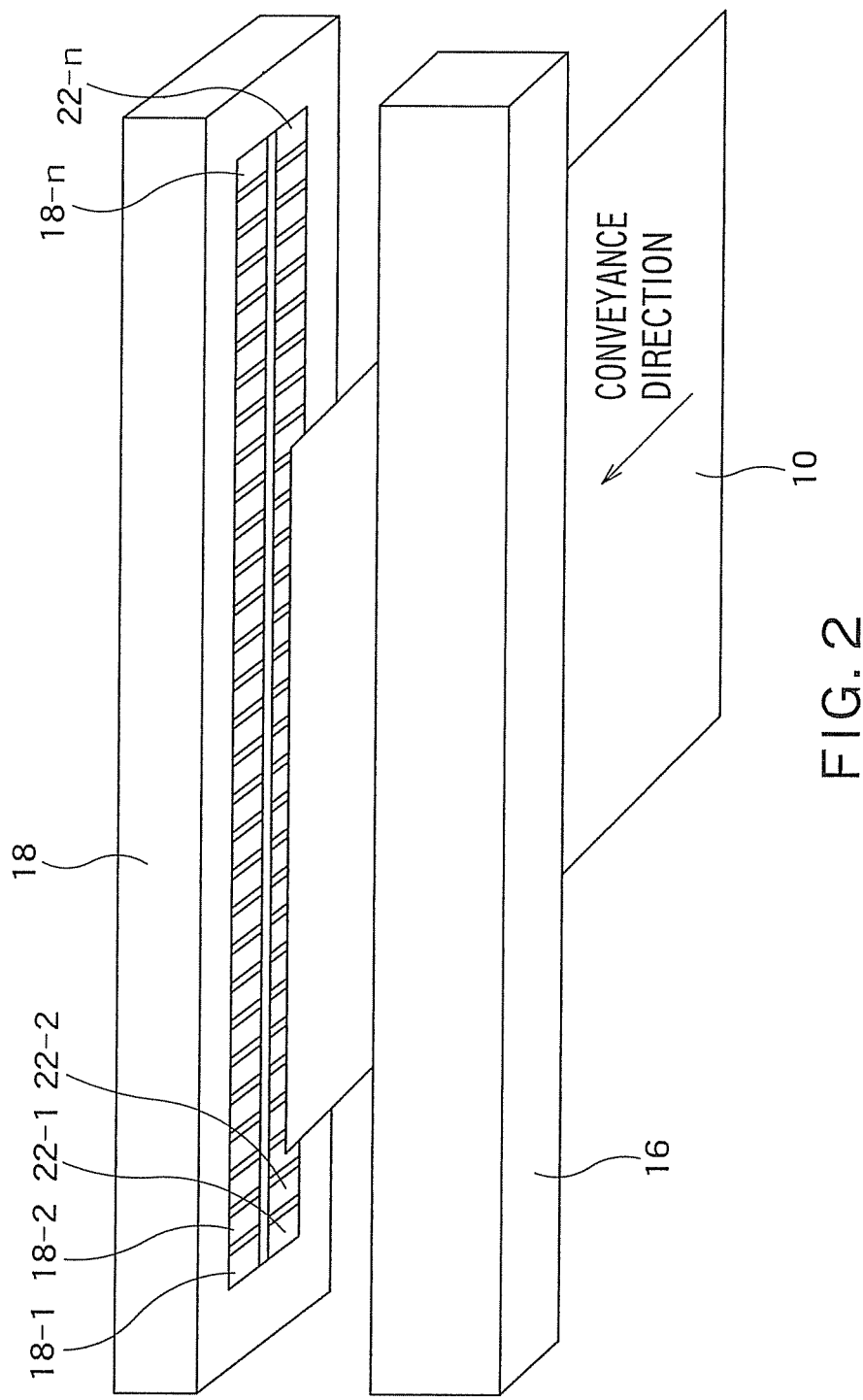
FIG. 2 is a perspective diagram showing an ultrasonic wave generator and a detecting array according to the first embodiment.

FIG. 2 is an enlarged view at the measurement position, and the present embodiment will be explained in further detail using this drawing.

The sound source 16 and the position/adhesive material detecting array are arranged to face each other in a noncontact manner, and are long in the direction perpendicular to the conveyance direction of the sheet 10 while having a width larger than that of the sheet 10.

The sound source 16 is an all-in-one ultrasonic transducer and emits ultrasonic waves having same phase to the adhesive material detecting array.

The adhesive material detecting array 18 used in the present embodiment is integrated with the position detecting array.

The position detecting array is formed of n number of ultrasonic transducers 22-1 ... 22-n arranged on the upper side (first line) in the conveyance direction of the sheet 10. The position detecting array is arranged to have a width larger than that of the sheet 10, and receives ultrasonic waves directly from the sound source before the sheet 10 enters the measurement region. The sound pressure of ultrasonic waves detected at this time is defined as the initial sound pressure. It is possible to detect when the sheet 10 proceeds into the measurement region since the sound pressure of ultrasonic waves irradiated to the sheet 10 entering the measurement region is considerably attenuated compared to the initial sound pressure.

Further, the position detecting array detects, in the middle part thereof, attenuated ultrasonic waves obtained when ultrasonic waves pass through the sheet 10, and detects, in the end parts thereof, the initial sound pressure obtained when ultrasonic waves do not pass through the sheet 10. Therefore, the size of the sheet 10 can be calculated by counting the ultrasonic transducers receiving the attenuated ultrasonic waves, by which the size of the sheet 10 can be identified.

Furthermore, relative positions between the adhesive material detecting array 18 and the sheet 10 can be identified by the conveyance speed of the sheet 10 and the time after the sheet 10 proceeds into the measurement region. In addition, it is also possible to identify the size and kind of the sheet 10 by measuring the time until the ultrasonic transducer receiving the attenuated ultrasonic waves measures the initial sound pressure again.

Note that the position detecting array (ultrasonic transducers 22-1 ... 22-n) can be removed and the adhesive material detecting array (ultrasonic transducers 18-1 ... 18-n) can be used both as the position detecting array.

During the sheet 10 is in the measurement region, each of a plurality of ultrasonic transducers 18-1 ... 18-n arranged on the lower side measures the sound pressure of ultrasonic waves passing through a corresponding region. Here, when the sheet 10 has an adhesive material, ultrasonic waves are attenuated by passing through the adhesive material. Therefore, the calculation result obtained by the calculation processor (standard sound pressure minus measured sound pressure) becomes a plus value. Based on the result, the judging unit judges that the sheet 10 has an adhesive material, and judges that the sheet 10 is not suitable for distribution when the value exceeds a predetermined reference value. On the other hand, when the sheet has a lost part, the calculation result becomes a minus value since the attenuation of sound pressure due to the sheet 10 is not caused and the initial sound pressure is detected. Thus, the judging unit judges that the sheet 10 has a lost part, and judges that the sheet 10 is not suitable for distribution when the value (absolute value) exceeds a predetermined reference value.

The present embodiment is characterized in that the adhesive material detecting unit is divided into a plurality of ultrasonic transducers 18A arranged in the width direction of the sheet 10.

An adhesive material is a mending tape for mending a torn part of the sheet 10, for example, and the mending tape is generally adheres to a small part of the sheet 10. Further, the sheet 10 may have a partially lost part. When the area of an adhesive material or a lost part is small compared to the surface of the ultrasonic transducer for receiving ultrasonic waves, the attenuation ratio of the received sound pressure due to the adhesive material is reduced and thus the detection sensitivity to the adhesive material is reduced.

In order to solve this problem, in the present embodiment, a plurality of ultrasonic transducers are arranged and thus each ultrasonic transducer has a smaller surface for receiving ultrasonic waves, by which the ratio of the area of an adhesive material to the receiving surface of each ultrasonic transducer can be increased. As a result, detection sensitivity to an adhesive material can be improved. Concretely, it is desirable that each ultrasonic transducer has a width of approximately 10 mm or smaller, more desirably 2 mm or smaller in the arrangement direction.

A Modification Example of the First Embodiment

When a foreign material is adhered around the end part of the sheet, detection sensitivity to the adhesive material is reduced, which makes difficult to correctly identify a small adhesive material. This modification example is a technique to improve detection sensitivity to an adhesive material around the end portion of the sheet 10. This modification example will be explained by using the drawings.

Figure 3:
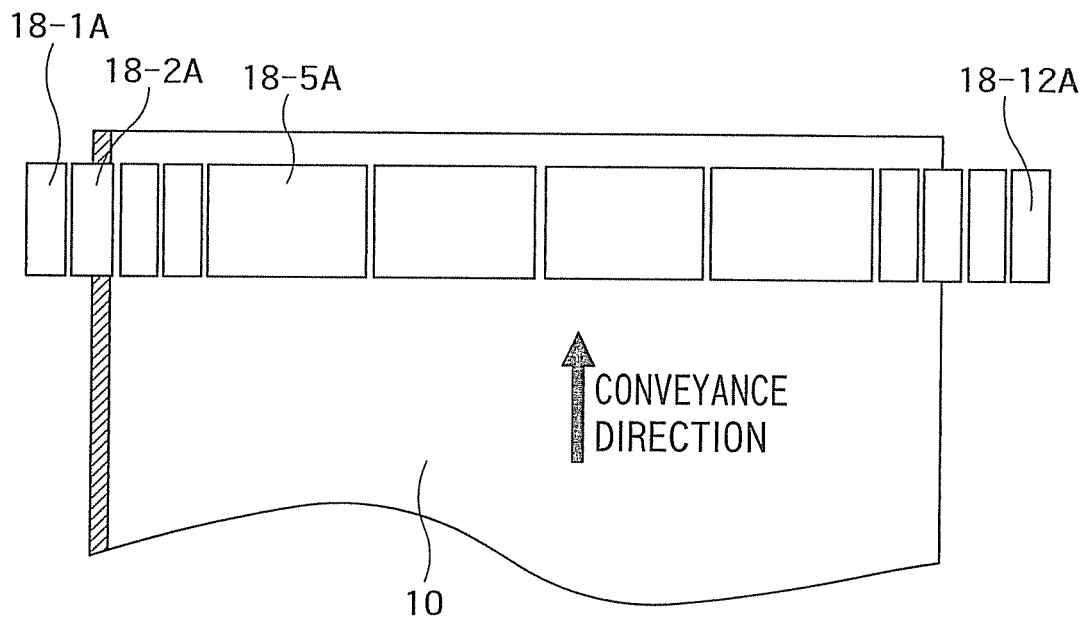
FIG. 3 is a schematic diagram showing a modification example of the detecting array.
Figure 4:
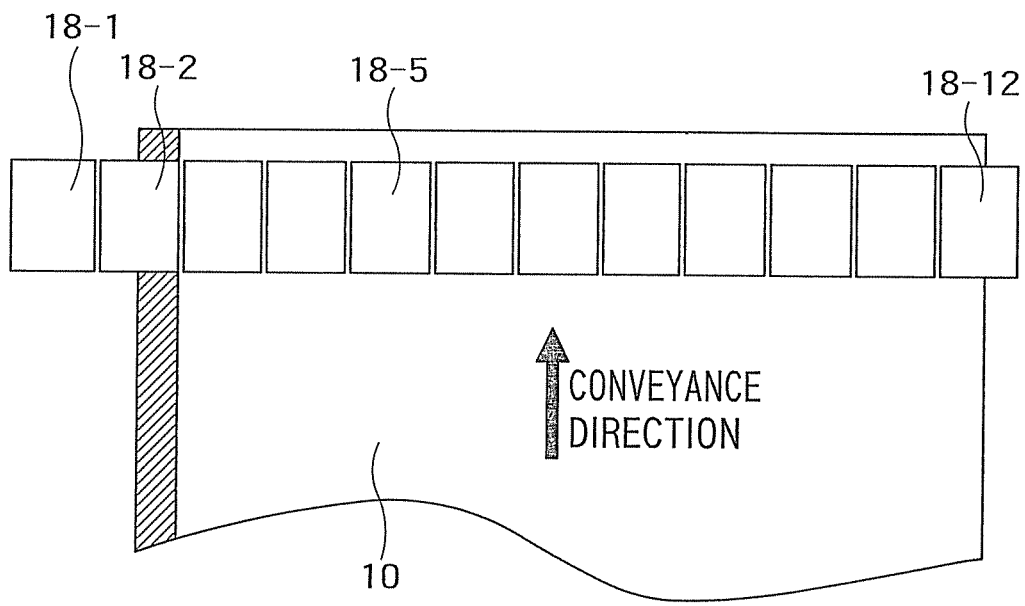
FIG. 4 is a schematic diagram of the detecting array according to the first embodiment.

Each of FIGS. 3 and 4 is a schematic diagram in which the ultrasonic transducers of the adhesive material detecting array and the sheet 10 are viewed from the ultrasonic transducer side. FIG. 3 shows the present modification example, while FIG. 4 shows the first embodiment for comparison.

The adhesive material detecting array shown in FIG. 3 has a plurality of ultrasonic transducers, in which ultrasonic transducers (18-1A to 18-4A and 18-9A to 18-12A) in the end parts have a small surface for receiving ultrasonic waves while ultrasonic transducers (18-5A to 18-8A) in the middle part have a large surface for receiving ultrasonic waves. The adhesive material detecting array shown in FIG. 4 has ultrasonic transducers all of which are the same in size of the surface for receiving ultrasonic waves, as similarly shown in the first embodiment.

As shown in the drawings, it is impossible to match the ends of the sheet 10 with the ultrasonic transducers since a gap is generated between the sheet 10 to be conveyed and the ultrasonic transducers in the arrangement direction of the ultrasonic transducers. FIG. 3 shows that the left end of the sheet 10 passes through the middle of the ultrasonic transducer 18-2A, while FIG. 4 shows that the left end of the sheet 10 passes through the middle of the ultrasonic transducer 18-2.

In the ultrasonic transducers 18-2 and 18-2A, a half of the receiving surface receives attenuated ultrasonic waves passing through the sheet 10, while the other half of the receiving surface receives the initial sound pressure obtained when ultrasonic waves do not pass through the sheet 10. Therefore, it is difficult for the ultrasonic transducers 18-2 and 18-2A arranged at the ends of the sheet 10 to detect the attenuation of ultrasonic waves caused by passing through the sheet 10. That is, it is difficult to detect an adhesive material in the region shown with oblique lines.

As shown in FIG. 3, small ultrasonic transducers arranged at the ends of the adhesive material detecting array reduce the region in which the attenuation of ultrasonic waves is difficult to measure, which makes it possible to correctly detect a further small adhesive material.

The sheet 10 has a lost part often in the end part and the adhesive material detecting array shown in this modification example is particularly effective for this case.

As stated above, by using a plurality of detecting elements, the size of each detecting element can be reduced and the ratio of the area of a foreign material adhering to the sheet (or a lost part) to the detection area of each detecting element can be increased, which makes it possible to improve detection accuracy and to detect and identify a small foreign material.

Furthermore, as stated above, the ultrasonic wave generator and the detecting array can be arranged in a noncontact manner. In addition, the ultrasonic wave generator and the detecting array can be arranged at different angles to the sheet while facing each other.

Furthermore, as stated above, a plurality of detecting elements for detecting sound pressure of the ultrasonic waves can be further arranged on an upper side in the conveyance direction in parallel with the detecting array. A detected position in the sheet by the detecting array may be specified by measuring a time elapsed after the sound pressure detected by the plurality of detecting elements has changed.

It is desirable that the detecting array has a width larger than that of the sheet and that the detecting elements arranged in the middle part of the detecting array have a width larger than that of the detecting elements arranged in the end parts of the detecting array.

With the above configuration, a foreign material adhering to the end part of a sheet and a lost part in the end part of the sheet can be detected more correctly.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A sheet processing device comprising:
an ultrasonic wave generator configured to irradiate ultrasonic waves to a sheet being conveyed, from one side of the sheet;
a first detecting array arranged on the other side of the sheet in a noncontact manner with the ultrasonic wave generator, configured to detect sound pressure of the ultrasonic waves passing through the sheet;
a judging unit configured to judge a state of the sheet by comparing a predetermined value with the sound pressure;
a second detecting array arranged on the other side of the sheet at a different position from that of the first detecting array in a conveyance direction of the sheet, configured to detect sound pressure of the ultrasonic waves passing through the sheet wherein the sheet being conveyed crosses first the second detecting array and then the first detecting array; and
a position detecting unit configured to detect a position of the sheet at which the first detecting array detects the sound pressure by measuring a time elapsed after the sound pressure detected by the second detecting array has changed.

2. The device according to claim 1, wherein
the first detecting array includes a plurality of detecting elements,
the first detecting array has a width larger than that by which the detecting array crosses the sheet and
the detecting elements arranged in the middle part of the first detecting array each have a width larger than that of the detecting elements arranged in the end parts of the detecting array.

* * * * *